United States Patent [19] [11] 4,356,024
Dickore' et al. [45] Oct. 26, 1982

[54] PROCESS FOR THE PREPARATION OF 1-AMINO-1,3,5-TRIAZINE-2,4(1H, 3H)-DIONE COMPOUNDS

[75] Inventors: Karlfried Dickore', Leverkusen; Engelbert Kühle, Berg.-Gladbach, both of Fed. Rep. of Germany

[73] Assignee: Bayer Aktiengesellschaft, Leverkusen, Fed. Rep. of Germany

[21] Appl. No.: 233,250

[22] Filed: Feb. 10, 1981

[30] Foreign Application Priority Data

Feb. 20, 1980 [DE] Fed. Rep. of Germany ....... 3006263

[51] Int. Cl.³ .................... C07D 251/38; A01N 43/64
[52] U.S. Cl. .......................................... 71/93; 71/90; 71/92; 542/425; 544/113; 544/2; 544/3; 544/5; 544/7; 544/8; 544/54; 544/58.6; 544/60; 544/63; 544/65; 544/66; 544/67; 544/96; 544/98; 544/223
[58] Field of Search ............... 71/93, 90, 92; 544/223, 544/113, 2, 3, 5, 7, 8, 54, 58.6, 60, 63, 65, 66, 67, 96, 98; 542/425

[56] References Cited

U.S. PATENT DOCUMENTS 3,907,796 9/1975 Lewell ............................... 260/249.5
4,056,527 11/1977 Schlee et al. ........................ 544/223

FOREIGN PATENT DOCUMENTS 34750 9/1981 European Pat. Off. .
2254200 5/1974 Fed. Rep. of Germany .
2311662 9/1974 Fed. Rep. of Germany .
2351556 4/1975 Fed. Rep. of Germany .
1344895 10/1963 France .

Primary Examiner—John M. Ford
Attorney, Agent, or Firm—Felfe & Lynch

[57] ABSTRACT

A process for the preparation of a 1-amino-1,3,5-triazine-2,4(1H, 3H)-dione compounds comprising the steps of reacting an N-substituted imido-dicarboxylic acid diaryl ester with an isothiosemicarbazone at a temperature of between 50° and 150° C. to form a 1-alkylidene-amino-1,3,5-triazine-2,4(1H, 3H)-dione reaction product; and thereafter, hydrolyzing the reaction product in an acid medium. The reaction product need not be separated from the reaction mixture before the hydrolysis step. Certain novel 1-amino-1,3,5-triazine-2,4(1H, 3H)-dione compounds are provided. The compounds are useful as herbicides.

13 Claims, No Drawings

PROCESS FOR THE PREPARATION OF 1-AMINO-1,3,5-TRIAZINE-2,4(1H, 3H)-DIONE COMPOUNDS

This invention relates to a process for the preparation of 1-amino-1,3,5-triazine-2,4-(1H, 3H)-dione compounds. In additional aspect, the invention relates to certain novel 1-amino-1,3,5-triazine-2,4(1H,3H)-dione compounds. Such compounds are useful as herbicides.

It is known that 1-amino-1,3,5-triazine-2,4(1H, 3H)-dione compounds can be prepared by reaction of imidodicarboxylic acid dichlorides with hydrohalides of isothiosemicarbazones and subsequent acid-catalyzed hydrolysis of the 1-alkylideneamino derivatives initially formed as intermediate products (see DE-OS (German Published Specification) No. 2,254,200). However, this process has a number of disadvantages. Thus, the use of imidodicarboxylic acid dichlorides as starting substances represents a considerable technical effort, since it is possible to prepare them only by multi-stage processes (see DE-OS (German Published Specification) No. 2,351,556) or via starting materials which are not readily accessible (see DE-OS (German Published Specification) No. 1,298,095), and in addition the yields are not satisfactory. Another disadvantage of the known process is that the cyclisation of imidodicarboxylic acid dichlorides with the hydrohalides of isothiosemicarbazones must be carried out in the presence of three mols of an organic base in an organic solvent. Carrying out this process on an industrial scale is additionally made more difficult by the recovery of the solvents and the bases which is necessary.

The present invention now provides a process for the preparation of a 1-amino-1,3,5-triazine-2,4(1H, 3H)-dione of the general formula:

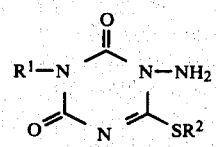

(I)

in which $R^1$ represents a saturated or unsaturated aliphatic or cycloaliphatic hydrocarbon radical, an araliphatic hydrocarbon radical or an aryl radical, each of which can carry one or more substituents selected from halogen, nitro, alkyl, alkoxy, alkylmercapto, halogenoalkyl, cyano, aryl, aryloxy and arylmercapto, or represents a heterocyclic radical and $R^2$ represents a saturated or unsaturated aliphatic or cycloaliphatic hydrocarbon radical, or an araliphatic hydrocarbon radical, each of which can carry one or more substituents selected from halogen, cyano, nitro, alkyl, alkoxy, alkoxycarbonyl and alkylmercapto, in which an N-substituted imido-dicarboxylic acid diaryl ester of the general formula:

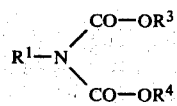

(II)

in which
  $R^1$ has the abovementioned meaning and
  $R^3$ and $R^4$ represent identical or different aryl radicals, each of which can carry one or more substituents selected from alkyl, alkoxy, halogen, halogenoalkyl, cyano and nitro, is reacted with an isothiosemicarbazone of the general formula:

(III)

in which:
  $R^2$ has the abovementioned meaning,
  $R^5$ represents hydrogen or an alkyl, cycloalkyl, aralkyl or aryl radical, each of which can be substituted by halogen, cyano, nitro, alkyl, alkoxy or alkylmercapto, and
  $R^6$ represents an alkyl, cycloalkyl, aralkyl or aryl radical, each of which can be substituted by halogen, cyano, nitro, alkyl, alkoxy or alkylmercapto, or
  $R^5$ and $R^6$, together with the alkylidene C atom represents a 5-membered to 7-membered carbocyclic ring,
at a temperature between 50° and 150° C. and the 1-alkylideneamino-1,3,5-triazine-2,4(1H, 3H)-dione thereby formed, of the general formula:

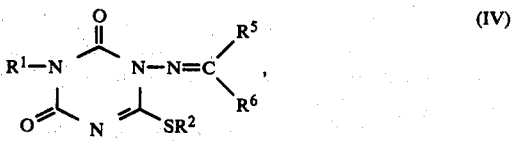

(IV)

in which $R^1$, $R^2$, $R^5$ and $R^6$ have the abovementioned meanings, is hydrolysed in an acid medium in a manner which is in itself known, if appropriate without being intermediately isolated.

The process according to the invention—which permits the preparation of the compounds (I) in high yields and in an industrially simple manner—has a number of surprising advantages. Thus, the reaction can be carried out in the melt of the starting materials without using solvents. No other auxiliaries, for example organic bases, are required in this procedure. The imidodicarboxylic acid diaryl esters used as starting substances in the process according to the invention can be prepared in a high yield in a simple manner from precursors which are readily available on an industrial scale.

If neopentyl-imido-dicarboxylic acid diphenyl ester and acetone S-ethyl-isothiosemicarbazone are used as starting substances, the course of the reaction can be represented by the following equation:

$(CH_3)_3C-CH_2-N(COOC_6H_5)_2 +$

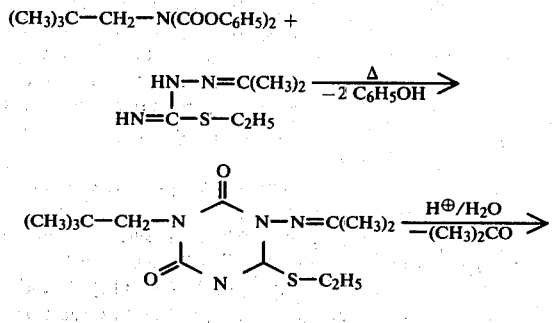

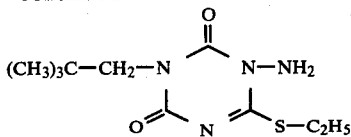

The formula (II) provides a general definition of the N-substituted imido-dicarboxylic acid diaryl esters to be used as starting substances. Preferably, in this formula, R¹ represents a straight-chain or branched alkyl radical which has 1–10 C atoms and can optionally be substituted by lower alkoxy, lower alkylmercapto, halogen (especially chlorine or fluorine), cyano or nitro; or an alkenyl radical with 3–8 C atoms, an alkynyl radical with 3–8 C atoms or a cycloaliphatic radical which has 5–8 ring C atoms, any of which can optionally be substituted by lower alkyl or lower alkoxy; an araliphatic radical with 7–12 C atoms, it being possible for the aromatic ring system optionally to be substituted by halogen, nitro, trihalogeno-lower alkyl (especially trifluoromethyl), cyano, lower alkyl, lower alkoxy or lower alkylmercapto; an aromatic radical which has 6–12 C atoms and can optionally be substituted by halogen, nitro, trihalogeno-lower alkyl (especially trifluoromethyl), cyano, lower alkyl, lower alkoxy or lower alkylmercapto; or a heterocyclic radical with 5–6 ring atoms, it being possible for 1–3 hetero-atoms (such as oxygen and/or sulphur and/or nitrogen) to be present in the ring system, and $R^3$ and $R^4$, which may be identical or different, each represent a phenyl radical, which can optionally carry one or more substituents selected from lower alkyl, lower alkoxy, halogen, halogeno-lower alkyl (especially trifluoromethyl), cyano and nitro, or a naphthyl radical.

The formula (III) provides a general definition of the isothiosemicarbazones also to be employed as starting substances. Preferably in this formula, $R^2$ represents a straight-chain or branched alkyl radical which has 1–6 C atoms and can optionally be substituted by lower alkoxy, lower alkylmercapto, lower alkoxycarbonyl, halogen, cyano or nitro; an alkenyl radical with 3–6 C atoms; an alkynyl radical with 3–6 C atoms; a cycloaliphatic radical which has 5–8 ring C atoms and can optionally be substituted by lower alkyl or lower alkoxy; or an araliphatic radical with 7–12 C atoms, it being possible for the aromatic ring system optionally to carry one or more substituents selected from lower alkyl, lower alkoxy, lower alkylmercapto, lower alkoxycarbonyl, halogen, cyano and nitro, $R^5$ represents hydrogen or alkyl with 1–3 C atoms, cycloalkyl with 5–7 C atoms, benzyl or an aryl radical with 6–10 C atoms, it being possible for each of these radicals to be substituted by halogen, cyano, nitro, lower alkyl, lower alkoxy or lower alkylmercapto, and $R^6$ represents alkyl with 1–3 C atoms, cycloalkyl with 5–7 C atoms, benzyl or aryl with 6–10 C atoms, it being possible for each of these radicals to be substituted by halogen, cyano, nitro, lower alkyl, lower alkoxy or lower alkylmercapto, or $R^5$ and $R^6$ form, together with the alkylidene C atom, a 5- to 7-membered carbocyclic ring.

$R^5$ and $R^6$ particularly preferably represent methyl.

The expressions "lower alkyl", "lower alkoxy", "lower alkylmercapto", "halogeno-lower alkyl" and the like in the context of this invention are intended to denote corresponding radicals with in each case 1–4 C atoms.

The N-substituted imido-dicarboxylic acid diaryl esters (II) used according to the invention as starting substances have not hitherto been described in the literature. However, they can be prepared in a simple manner by a process which does not belong to the state of the art (but which is the subject of another application for protection), by reacting carbamic acid aryl esters of the general formula:

in which $R^1$ and $R^3$ have the abovementioned meaning, with carbonic acid aryl ester halides of the general formula:

in which:

$R^4$ has the abovementioned meaning and

X represents halogen, for example chlorine, if appropriate in the presence of a diluent, but in the absence of an acid-binding agent, at a temperature between 100° and 300° C., preferably between about 170° and 250° C., the carbonic acid aryl ester halides (VI) preferably being employed in amounts greater than the stoichiometric amount.

The carbamic acid aryl esters of the formula (V) are already known, or they can be prepared by known processes by addition of isocyanates onto phenols (see Houben-Weyl, Methoden der organischen Chemie (Methods of Organic Chemistry), 4th edition, volume 8, page 142 (1952)) or by reaction of carbonic acid aryl ester chlorides with primary amines (see Houben-Weyl, Methoden der organischen Chemie (Methods of Organic Chemistry), 4th edition, volume 8, page 138 (1952), and the preparation examples). The starting compounds of the formula (V) can furthermore be prepared by reaction of carbonic acid diaryl esters with amines (see Houben-Weyl, Methoden der organischen Chemie (Methods of Organic Chemistry), 4th edition, volume 8, page 139 (1952)).

The carbonic acid aryl ester halides (VI) are likewise already known, or they can be prepared by known processes. Thus, for example, the carbonic acid phenyl ester chlorides can be prepared in a manner which is in itself known by phosgenation of phenols (see Houben-Weyl, Methoden der organischen Chemie (Methods of Organic Chemistry), 4th edition, volume 8, page 103 (1952)); the corresponding carbonic acid phenyl ester fluorides can be obtained analogously from phenols and difluorophosgene (see J. Chem. Soc. [London] 1948, page 2183).

The imido-dicarboxylic acid diaryl esters (II) are isolated in a simple manner by separating the reaction mixture by distillation; solid, higher-melting derivatives can furthermore easily be purified by recrystallisation.

Specific examples which may be mentioned of the N-substituted imido-dicarboxylic acid diaryl esters (II) which can be used according to the invention are: phenyl, 2-chlorophenyl, 4-chlorophenyl, 4-methylphenyl, 4-methoxyphenyl, 4-nitrophenyl, 1-naphthyl or 2-naphthyl esters, the two aryl radicals being identical or different, of methyl-, ethyl-, 2-chloroethyl-, 2,2,2-trifluoroethyl-, propyl-, isopropyl-, tert.-butyl-, sec.-butyl-, isobutyl-, pentyl-, isopentyl-, neopentyl-, 1-ethylpropyl-, 1,2,2-trimethylpropyl-, 2-ethoxymethyl-, 2-ethylmercaptoethyl-, ω-cyanohexyl-, allyl-, propargyl-, cyclopropylmethyl-, cyclopentylmethyl-, cyclohexylmethyl-, (2,5-methano-cyclohexyl)-methyl-, cycloheptylmethyl-, cyclododecanylmethyl-, adamantylmethyl-, 2-furylmethyl-, 2-pyranylmethyl-, 2-pyridylmethyl-, 3-pyridylmethyl-, 4-pyridylmethyl-, 2-methylpentyl-, 2-ethylpentyl-, 2-methylhexyl-, 2-ethylhexyl-, cyclopentyl-, cyclohexyl-, 2-methyl-cyclohexyl-, benzyl-, 4-chlorobenzyl-, 4-nitrobenzyl-, phenethyl-, phenyl-, 3-chlorophenyl-, 4-chlorophenyl-, 3,5-dichlorophenyl-, 3,4-dichlorophenyl-, 3-trifluoromethylphenyl-, 2-chloro-4-nitro-phenyl-, 3-methylphenyl-, 4-methylphenyl-, 3-methoxy-phenyl-, 1-naphthyl-, 2-furyl-, 4-pyridyl-, 2-thienyl, 2-benzthiazolyl- or 2-benzimidazolylimido-dicarboxylic acid.

The isothiosemicarbazones of the formula (III) also to be used according to the invention as starting substances are likewise known, or they can be prepared by known processes, for example by S-alkylation of thiosemicarbazones (see Houben-Weyl, Methoden der organischen Chemie (Methods of Organic Chemistry), 4th edition, volume 9, page 912).

Specific examples of those isothiosemicarbazones (III) which may be mentioned are: acetone S-methyl-, acetone S-ethyl-, acetone S-benzyl-, acetone S-carbomethoxymethyl-, isobutyraldehyde S-methyl-, benzaldehyde S-methyl-, benzaldehyde S-2-chloroethyl-, acetone S-allyl-, acetone S-propargyl-, acetone S-methoxymethyl-, acetone S-cyanomethyl-, cyclopentanone S-methyl-, cyclohexanone S-ethyl-, cyclohexanone S-carbethoxymethyl-, cycloheptanone S-ethyl-, acetophenone S-ethyl-, benzophenone S-methyl-, butan-2-one S-4-chlorobenzyl- or butan-2-one S-ethyl-isothiosemicarbazone.

The first stage of the process according to the invention, that is to say the cyclisation reaction (II)+(III)→(IV), is preferably carried out in a melt of the starting materials, without a diluent. However, it is also possible to carry out this reaction in the presence of an inert organic solvent as the diluent. Possible inert organic solvents for this are hydrocarbons, for example toluene, chlorinated hydrocarbons, for example chlorobenzene, and alcohols, for example isopropanol and sec.-butanol.

The reaction temperatures can be varied within a substantial range in this process stage. As indicated above, the reaction is in general carried out at temperatures between 50° and 150° C., preferably between 70° and 120° C. It is generally not necessary to apply increased pressure.

In carrying out the first stage of the process according to the invention, in general 0.9–1.1 moles of the isothiosemicarbazone of the formula (III) are employed per mole of the imido-dicarboxylic acid diarylester of the formula (II). The components are preferably reacted in a stoichiometric molar ratio of 1:1, by a procedure in which one of the components is melted, the other is added and the mixture is kept at elevated temperature until the reaction has ended. The course of the reaction can easily be followed by monitoring by gas chromatography.

If desired, the 1-alkylideneamino-1,3,5-triazine-2,4(1H, 3H)-diones of the formula (IV) formed as intermediate products can be intermediately isolated. The intermediate products (IV) can be worked up and isolated, for example, by a procedure in which the optionally substituted phenol or phenol mixture formed in the cyclisation reaction is distilled off in vacuo and the residue is purified, if necessary, by distillation under a high vacuum or by recrystallisation.

Subsequent hydrolysis to split off the alkylidene radical (=CR$^5$R$^6$) serving as the protective group, that is to say (IV)→(I), is carried out in an acid medium in a manner which is in itself known (see, for example, DE-OS (German Published Specification) No. 2,254,200 and U.S. Pat. No. 4,056,527). It is particularly expedient to dissolve the intermediate products (IV) in an alcohol, for example isopropanol, to add a catalytic amount of an acid, for example a mineral acid, such as sulphuric acid, or an organic sulphonic acid, such as p-toluenesulphonic acid, at a temperature between about 40° and 70° C., if appropriate under reduced pressure, and to distil off the carbonyl compound formed, of the formula R$^5$—CO—R$^6$, from the reaction mixture together with some of the alcohol employed as the diluent. The end products (I) are isolated in a known manner by crystallising out and filtering off; for further purification, the end products (I) can easily be recrystallised.

The 1-amino-1,3,5-triazine-2,4(1H, 3H)-diones (I) which can be prepared according to the invention are known in most cases and they have excellent herbicidal properties (see, for example, DE-OS (German Published Specification) No. 2,254,200; U.S. Pat. No. 4,056,527; and also Danish Patent Specification No. 136,067).

The 1-alkylideneamino-1,3,5-triazine-2,4(1H, 3H)-diones (IV), some of which are new, formed in the first stage of the process according to the invention are not only of interest as intermediate products for the preparation of the corresponding 1-amino compounds (I), but moreover also can still have a pronounced herbicidal activity (with regard to the known compounds of the general formula (IV) see DE-OS (German Published Specification) No. 2,254,200; U.S. Pat. No. 4,056,527; and Danish Patent Specification No. 136,067).

In principle, the new compounds of the general formula (IV) can be formulated and used in the same manner as the compounds which are already known.

It is furthermore possible to replace the SR$^2$ radicals in the 6-position of the compounds of the general formula (I) and (IV) by alkylamino or dialkylamino groups by reaction with primary or secondary amines, herbicidal active compounds which are also known being obtained (again, see the abovementioned publications: DE-OS (German Published Specification) No. 2,254,200; U.S. Pat. No. 4,056,527; and Danish Patent Specification No. 136,067).

The following preparative examples are intended to illustrate the invention in more detail.

PREPARATIVE EXAMPLES

EXAMPLE 1

(a) 1st stage:

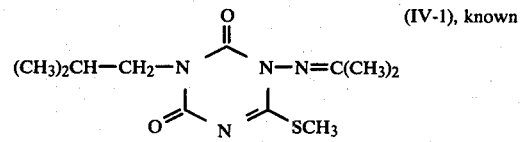

(IV-1), known 34.6 g (0.11 mol) of N-isobutyl-imido-dicarboxylic acid diphenyl ester (II-1) and 16.0 g (0.11 mol) of acetone S-methyl-isothiosemicarbazone were melted at 50° C. and the melt was stirred for 4 hours in an oil bath of 100° C. The phenol formed was distilled off under a pressure of 18 mbars, the bath temperature being increased to 140° C. The residue (30.3 g) solidified; it was boiled up with 150 ml of cyclohexane, 22.4 g of pure 1-isopropylideneamino-3-isobutyl-6-methylthio-1,3,5-triazine-2,4(1H, 3H)-dione (IV-1) of melting point 125°–127° C. remaining as undissolved material. A further 6.4 g of (IV-1) crystallised out of the filtrate from the mixture. The total yield was 28.8 g (97% of theory). The compound (IV)-1) could be distilled; boiling point: 165° C. under 0.38 mbar.

(b) 2nd stage:

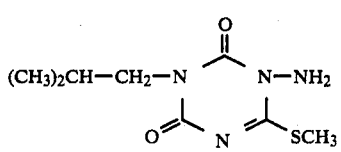
(I-1), known 27.0 g (0.1 mol) of the compound (IV-1) were dissolved in 200 ml of isopropanol at 60° C. in a distillation apparatus and a pressure of 260–200 mbar was established, so that the solvent started to boil and was condensed in the descending condenser. The internal temperature was then 45°–50° C. A solution of 0.4 ml of concentrated sulphuric acid in 7 ml of water was then added dropwise in the course of 15 minutes, about 70 ml of isopropanol being distilled off during this period, together with the acetone formed. 14.5 g of 1-amino-3-isobutyl-6-methylthio-1,3,5-triazine-2,4(1H, 3H)-dione (I-1) of melting point 167°–169° C. crystallised out, at 0° C., from the solution which remained; a further 4.5 g were obtained from the concentrated filtrate of the mixture. The total yield of 19.0 g corresponding to 83% of theory.

(c) The starting material of the formula (II-1) could be prepared as follows:

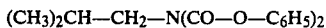

600 ml (4.72 mol) of carbonic acid phenyl ester chloride were brought to the boil in a 4-necked flask provided with a stirrer, gas inlet tube, reflux condenser and dropping funnel, whilst passing through a stream of air or nitrogen. A solution of 77.2 g (0.4 mol) of isobutylcarbamic acid phenyl ester (melting point: 67° C.) in 300 ml (2.36 mol) of carbonic acid phenyl ester chloride was then uniformly added dropwise at an internal temperature of 180°–185° C. in the course of 5 hours, air or nitrogen further being passed through the reaction solution for rapid removal of the hydrogen chloride formed. The mixture was subsequently stirred for a further 2 hours at the boiling point, the excess carbonic acid phenyl ester chloride was distilled off at a bath temperature of 140° C. and under a pressure of 20 mbar and the residue was distilled in vacuo.

102.4 g of N-isobutyl-imido-dicarboxylic acid diphenyl ester with a boiling point of 160° C./0.1 mbar and a purity of 93.7% were obtained. After recrystallising from about 500 ml of petroleum ether, filtering off the crystals at −70° C. and washing them with intensely cooled petroleum ether, 88 g of the given compound with a melting point of 40° C. and a purity of 100%, corresponding to 70% of theory, were obtained.

EXAMPLE 2

(a) 1st stage:

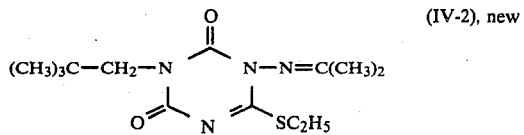
(IV-2), new

The intermediate product (IV-2), that is to say 1-isopropylideneamino-6-ethylthio-3-neopentyl-1,3,5-triazine-2,4(1H, 3H)-dione, could be prepared and isolated analogously to Example (1a); melting point: 100°–102° C., boiling point: 176° C./0.4 mbar.

(b) 2nd stage:

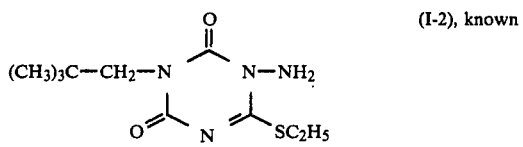
(I-2), known

The compound (I-2), that is to say 1-amino-6-ethylthio-3-neopentyl-1,3,5-triazine-2,4(1H, 3H)-dione, could be prepared analogously to Example 1b); melting point: 202°–204° C.

However, it was also possible to prepare the compound (I-2) in the following manner, without intermediate isolation of (IV-2):

A mixture of 65.4 g (0.2 mol) of N-neopentylimidodicarboxylic acid diphenyl ester (II-2) and 31.8 g (0.2 mol) of acetone S-ethyl-isothiosemicarbazone (III-2) was melted under nitrogen and the melt was stirred at 100° C. for 5 hours. The phenol formed was then distilled off in vacuo.

The residue, which essentially consisted of 1-isopropylideneamino-6-ethylthio-3-neopentyl-1,3,5-triazine-2,4(1H, 3H)-dione (IV-2), was dissolved in 200 ml of isopropanol. To split off the isopropylidene protective group hydrolytically, 2.8 g of p-toluenesulphonic acid were added, and 14.4 ml of water were added dropwise at a temperature of 60° C. and under a pressure of 200–300 mbar in the course of half an hour. The acetone formed was distilled off during the reaction, together with about 100 ml of isopropanol. The 1-amino-6-ethylthio-3-neopentyl-1,3,5-triazine-2,4-(1H, 3H)-dione (I-2) which had crystallised out was filtered off at 0° C. and washed with methanol. 38.2 g of (I-2) of melting point 202° C., corresponding to a yield of 74% of theory, were obtained.

(c) The starting material of the formula (II-2) could be prepared as follows:

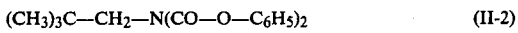

A solution of 331 g (1.6 mol) of neopentylcarbamic acid phenyl ester in 1,000 g (6.39 mol) of carbonic acid phenyl ester chloride was added dropwise to 4,000 g (25.56 mol) of boiling carbonic acid phenyl ester chloride, through which a vigorous stream of nitrogen was passed, in the course of 5 hours. The overhead temperature of the reflux condenser was kept at 80°–90° C., so that the small amount of neopentyl isocyanate formed as a by-product could be distilled off over the top with the stream of nitrogen and could be condensed in a subsequent descending condenser. (After reaction with phenol to give neopentyl-carbamic acid phenyl ester, this was then passed again to the reaction). The mixture was stirred for 4 hours, whilst passing further nitrogen through, the excess carbonic acid phenyl ester chloride was then distilled off at a bath temperature of 140° C. and under a pressure of 20 mbar and the residue was distilled, from a heating bath of 170° C., until the boiling point had reached 150° C. under a pressure of 0.6 mbar. The residue consisted of 96.5% pure N-neopentyl-imido-dicarboxylic acid diphenyl ester. Yield: 489 g (90% of theory). A sample recrystallised from petroleum ether melted at 81° C. The substance could be distilled; boiling point: 156° C./0.02 mbar.

The neopentyl-carbamic acid phenyl ester which was used as the starting compound, and which had not hitherto been described in the literature, could be prepared, for example, as follows, starting from neopentylamine:

A solution of 80 g (2 mol) of sodium hydroxide and 176 g (2 mol) of 99% pure neopentylamine in 3.4 liters of water was added dropwise to a solution of 329 g (2.1 mol) of carbonic acid phenyl ester chloride in 1 liter of toluene, whilst stirring vigorously. An internal temperature of 10°-20° C. was maintained by cooling. When the reaction had ended, the phases were separated, the organic phase was washed with water and filtered and the filtrate was evaporated to dryness. 408 g of a 97% pure crude product (95.6% of theory) of melting point 69°-72° C. which was sufficiently pure for further reactions were obtained. After recrystallising from 2 liters of petroleum ether, 65 g of melting point 77°-78° C. were obtained.

The following 1-alkylideneamino-1,3,5-triazine-2,4(1H, 3H)-diones (IV) could be prepared analogously to Example (1a):

| Example No. | Structural formula | Compound No. | Melting point (boiling point) | Known/new |
|---|---|---|---|---|
| (3a) | CH₃—N, O, N—N=C(CH₃)(CH₃), O, N, S—CH₃ | (IV-3) | 130–131° C. | known |
| (4a) | CH₃—N, O, N—N=C(CH₃)(CH₃), O, N, S—C₂H₅ | (IV-4) | 121–122° C. (173° C./0,5 mbar) | known |
| (5a) | (CH₃)₂CH—N, O, N—N=C(CH₃)(CH₃), O, N, S—CH₃ | (IV-5) | 110–112° C. | known |
| (6a) | (CH₃)₃C—CH₂—N, O, N—N=C(CH₃)(CH₃), O, N, S—CH₃ | (IV-6) | 122–124° C. | new |
| (7a) | CF₃—CH₂—N, O, N—N=C(CH₃)(CH₃), O, N, S—CH₃ | (IV-7) | 142° (145–150° C./0,3 mbar) | new |
| (8a) | CF₃—CH₂—N, O, N—N=C(CH₃)(CH₃), O, N, S—C₂H₅ | (IV-8) | 112–114° C. | new |
| (9a) | cyclopropyl-N, O, N—N=C(CH₃)(CH₃), O, N, S—CH₃ | (IV-9) | 107–109° C. | new |

| Example No. | Structural formula | Compound No. | Melting point (boiling point) | Known/new |
|---|---|---|---|---|
| (10a) | (cyclohexyl-H)-N—C(=O)—N(—N=C(CH₃)(CH₃))—C(=S-CH₃)=N—C(=O) ring | (IV-10) | 111–112° C. | known |

The following 1-amino-1,3,5-triazine-2,4(1H, 3H)-diones (I) could be prepared analogously to Example (1b) or (2b):

| Example No. | Structural formula | Compound No. | Melting point | Known/new |
|---|---|---|---|---|
| (3b) | CH₃—N ring with N—NH₂, S—CH₃ | (I-3) | 174–175° C. | known |
| (4b) | CH₃—N ring with N—NH₂, S—C₂H₅ | (I-4) | 133–134° C. | new |
| (5b) | (CH₃)₂CH—N ring with N—NH₂, S—CH₃ | (I-5) | 148–150° C. | known |
| (6b) | (CH₃)₃C—CH₂—N ring with N—NH₂, S—CH₃ | (I-6) | 229–231° C. | known |
| (7b) | CF₃—CH₂—N ring with N—NH₂, S—CH₃ | (I-7) | 147–150° C. | new |
| (8b) | CF₃—CH₂—N ring with N—NH₂, S—C₂H₅ | (I-8) | 135–137° C. | new |
| (9b) | cyclopropyl-N ring with N—NH₂, S—CH₃ | (I-9) | 158–159° C. | new |

| Example No. | Structural formula | Compound No. | Melting point | Known/ New |
|---|---|---|---|---|
| (10b) | (phenyl-H)–N(C=O)(N-NH₂)(C(=O)-O)(N)(C-S-CH₃) fused ring | (I-10) | 177–179° C. | known |

The following imido-dicarboxylic acid diaryl esters (II) could be prepared analogously to Example (1c):

| Example No. | Structural formula | Compound No. | Melting point |
|---|---|---|---|
| (3c) (4c) | CH₃—N(CO—O—C₆H₅)₂ | (II-3) | 102–105° C. |
| (5c) | (CH₃)₂CH—N(CO—O—C₆H₅)₂ | (II-5) | 35–37° C. |
| (2c) (6c) | (CH₃)₃C—CH₂—N(CO—O—C₆H₅)₂ | (II-2) | 81° C. (see Example 2c) |
| (7c) (8c) | CF₃—CH₂—N(CO—O—C₆H₅)₂ | (II-7) | 76° C. |
| (9c) | (H-phenyl)—N(CO—O—C₆H₅)₂ | (II-9) | 53° C. |
| (10c) | (H-phenyl)—N(CO—O—C₆H₅)₂ | (II-10) | 85° C. |

As stated above, the compounds prepared by the process according to the present invention have herbicidal properties.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleccharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseclus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

For combating weeds, the active compounds according to the invention can be used, as such or in their formulations, in admixture with other herbicides, it being possible to use finished formulations or tank mixing.

The active compounds can be converted into the customary formulations, such as solutions, emulsions, suspensions, powders, foams, granules, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, bird repellants, growth factors, plant nutrients and agents which improve soil structure.

The active compounds can be used as such, in the form of their formulations or in the use forms prepared therefrom by further dilution, such as ready-to-use solutions, suspensions, emulsions, powders and granules. They may be used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg/ha.

The present invention also provides a herbicidal composition containing as active ingredient a compound prepared by the process of the present invention in admixture with a solid diluent or carrier or in admixture with a liquid diluent or carrier containing a surface-active agent.

The present invention also provides a method of combating weeds which comprises applying to the weeds, or to a habitat thereof, a compound prepared by the process of the present invention alone or in the form of a composition containing as active ingredient such a compound in admixture with a diluent or carrier.

The present invention further provides crops protected from damage by weeds by being grown in areas in which immediately prior to and/or during the time of the growing a compound prepared by the process of the present invention was applied alone or in admixture with a diluent or carrier.

It will be seen that the usual methods of providing a harvested crop may be improved by the present invention.

The herbicidal activity of the compounds of this invention is illustrated by the following biotest Examples.

In these Examples, the compounds according to the present invention are each identified by the number (given in brackets) of the corresponding preparative Example.

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, compounds (IV-2), (IV-6), (IV-7), (IV-8), (IV-9), (I-4), (I-7), (I-8) and (I-9) showed an excellent action.

EXAMPLE B

Post-emergence Test
Solvent: 5 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was then diluted with water to the desired concentration.

Test plants which had a height of 5-15 cm were sprayed with the preparation of the active compound in such a way as to apply the amounts of active compound per unit area which were prescribed. The concentration of the spray liquor was so chosen that the amounts of active compound prescribed were applied in 2,000 l of water/ha. After three weeks, the degree of damage to the plants was rated in % damage in comparison to the development of the untreated control. The figures denoted:

0% = no action (like untreated control)
100% = total destruction.

In this test also, compounds (IV-2), (IV-6), (IV-7), (IV-8), (IV-9), (I-4), (I-7), (I-8) and (I-9) showed an outstanding action.

It will be understood that the specification and examples are illustrative, but not limitative of the present invention and that other embodiments within the spirit and scope of the invention will suggest themselves to those skilled in the art.

What is claimed is:

1. Process for the preparation of a 1-amino-1,3,5-triazine-2,4(1H, 3H) dione compound of the formula:

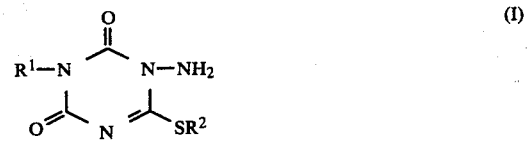

(I)

wherein:

R¹ represents a straight-chain or branched alkyl radical which has 1-10 carbon atoms and is optionally substituted by lower alkoxy, lower alkylmercapto, halogen, cyano or nitro; or an alkenyl radical with 3-8 carbon atoms, an alkynyl radical with 3-8 carbon atoms or a cycloaliphatic radical which has 5-8 ring carbon atoms, any of which is optionally substituted by lower alkyl or lower alkoxy; an araliphatic radical with 7-12 carbon atoms, the aromatic ring system of which being optionally substituted by halogen, nitro, trihalogeno-lower alkyl, cyano, lower alkyl, lower alkoxy or lower alkylmercapto; an aromatic radical which has 6-12 carbon atoms and is optionally substituted by halogen, nitro, trihalogeno-lower alkyl, cyano, lower alkyl, lower alkoxy or lower alkylmercapto; or a heterocyclic radical with 5-6 ring atoms, optionally containing 1-3 hetero-atoms selected from oxygen and/or sulphur and/or nitrogen, in the ring system, and R² represents a straight-chain or branched alkyl radical which has 1-6 carbon atoms and is optionally substituted by lower alkoxy, lower alkylmercapto, lower alkoxycarbonyl, halogen, cyano or nitro; an alkenyl radical with 3-6 carbon atoms; an alkynyl radical with 3-6 carbon atoms; a cycloaliphatic radical which has 5-8 ring carbon atoms and is optionally substituted by lower alkyl or lower alkoxy; or an araliphatic radical with 7-12 carbon atoms, the aromatic ring system of which optionally carrying substituents selected from lower alkyl, lower alkoxy, lower alkylmercapto, lower alkoxycarbonyl, halogen, cyano and nitro, which process comprises reacting an N-substituted imido-dicarboxylic acid diaryl ester of the formula:

in which:

R¹ has the same meaning as above, and

R³ and R⁴, which may be identical or different, each represent a phenyl radical optionally carrying substituents selected from lower alkyl, lower alkoxy, halogen, halogeno-lower alkyl, cyano and nitro, or a naphthyl radical, with an isothiosemicarbazone of the formula:

in which:

R² is identified as above,

R⁵ represents hydrogen or alkyl with 1-3 carbon atoms, cycloalkyl with 5-7 carbon atoms, benzyl or an aryl radical with 6-10 carbon atoms each of these radicals being optionally substituted by halogen, cyano, nitro, lower alkyl, lower alkoxy or lower alkylmercapto, and R⁶ represents alkyl with 1-3 carbon atoms, cycloalkyl with 5-7 carbon atoms, benzyl or aryl with 6-10 carbon atoms each of these radicals being optionally substituted by halogen, cyano, nitro, lower alkyl, lower alkoxy or lower alkylmercapto, or R⁵ and R⁶, together with the alkylidene carbon atom, represent a 5-membered to 7-membered carbocyclic ring, at a temperature between 50° and 150° C. and hydrolyzing, in acid medium, the 1-alkylideneamino-1,3,5-triazine-2,4(1H, 3H)-dione thereby formed of the formula:

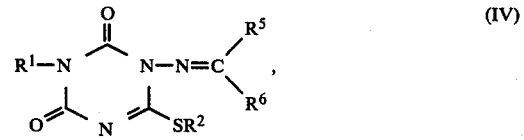

in which R¹, R², R⁵ and R⁶ are identified as above.

2. Process as claimed in claim 1 wherein said 1-alkylideneamino-1,3,5-triazine-2,4(1H, 3H)-dione is intermediately isolated.

3. Process as claimed in claim 1 wherein said 1-alkylideneamino-1,3,5-triazine-2,4(1H, 3H)-dione is not intermediately isolated.

4. Process as claimed in claim 1 wherein the reaction between Compounds (II) and (III) is carried out at a temperature between 70° and 120° C.

5. Process as claimed in claim 1 wherein 0.9 to 1.1 moles of the isothiosemicarbazone (III) are employed per mole of the imidodicarboxylic acid diaryl ester (II).

6. Process as claimed in claim 3 wherein 1 mole of the isothiosemicarbazone (III) is employed per mole of the imidodicarboxylic acid diaryl ester (II).

7. Process as claimed in claim 1 wherein the reaction between Compounds (II) and (III) is effected in the absence of a diluent.

8. Process as claimed in claim 1 wherein Compound (IV) is hydrolyzed in the presence of an alcohol as a solvent, and in the presences of a catalytic amount of an acid, at a temperature of between 40° and 70° C.

9. Process as claimed in claim 8 wherein the acid is sulfuric acid.

10. Process as claimed in claim 8 wherein the acid is p-toluenesulphonic acid.

11. 1-alkylideneamino-1,3,5-triazine-2,4(1H, 3H)-dione of the formula:

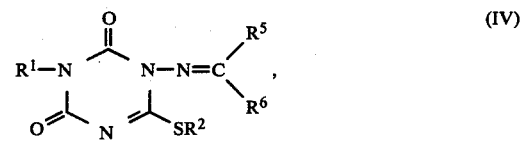

wherein:

(a) R¹ is neopentyl, R² is ethyl and R⁵ and R⁶ each represent methyl;

(b) R¹ is neopentyl and R², R⁵ and R⁶ each represent methyl;

(c) R¹ is 2,2,2-trifluoroethyl and R², R⁵ and R⁶ each represent methyl;

(d) R¹ is 2,2,2-trifluoroethyl, R² is ethyl and R⁵ and R⁶ each represent methyl; or (e) R¹ is cyclopentyl and R², and R⁵ and R⁶ each represent methyl.

12. Herbicidal composition comprising an agriculturally acceptable carrier and, as an active ingredient, a compound as claimed in claim 11.

13. Method of combating weeds, which method comprises applying to the weeds or their habitat, an effective amount of a compound as claimed in claim 11.

* * * * *